US00PP31959P2

(12) United States Plant Patent
Bradford et al.

(10) Patent No.: US PP31,959 P2
(45) Date of Patent: Jul. 14, 2020

(54) PLUM TREE NAMED 'BLACKRED VII'

(50) Latin Name: *Prunus salicina*
Varietal Denomination: Blackred VII

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 16/501,441

(22) Filed: Apr. 17, 2019

(51) Int. Cl.
*A01H 5/08* (2018.01)
*A01H 6/74* (2018.01)

(52) U.S. Cl.
USPC ..... Plt./184
CPC ..... *A01H 6/7472* (2018.05)

(58) Field of Classification Search
USPC ..... Plt./184
CPC ..... A01H 6/7472; A01H 5/08
See application file for complete search history.

(56) References Cited

U.S. PATENT DOCUMENTS

PP18,668 P2 3/2008 Bradford

OTHER PUBLICATIONS

Addenddum to Export Inspection Certificate for Stone Fruit, Feb. 2, 2018, pp. 1 and 42.*

* cited by examiner

*Primary Examiner* — Keith O. Robinson

(57) ABSTRACT

The present invention relates to a plum tree and more particularly to a new and distinct variety broadly characterized by a medium to large size, vigorous, hardy, and very productive tree. Being self-unfruitful, the present variety requires cross pollination from another plum or interspecific tree that blooms during the mid to late season, such as 'Plumsweet V' interspecific tree (U.S. Plant Pat. No. 16,369). The present variety's moderate amount of blossoms and strong pollen production entices strong bee activity to facilitate pollination. The fruit matures under the ecological conditions described during the first week of August, with first picking on Aug. 1, 2018. The fruit is medium is size, very oblate in shape, black in skin color, clingstone in type, mostly red in flesh color, firm in texture, juicy, and very good in flavor.

1 Drawing Sheet

Botanical classification: *Prunus salicina.*
Variety denomination: 'BLACKRED VII'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of plum tree, which has been denominated varietally as 'Blackred VII'.

During a typical blooming season we isolate as seed parents both individual and groups of different plum and interspecific trees by covering them with screen houses. A hive of bees is placed inside each such house, and bouquets to provide pollen from different plum, apricot, and interspecific hybrid trees are placed in buckets near the trees approximately every two days for the duration of the bloom. During 2001 one such house containing '19P442' plum tree (unpatented) was crossed by us in this manner. To pollinate this plum tree, we selected bouquets from several sources of plum trees without keeping specific written details. Upon reaching maturity the fruit from this plum tree was harvested, and the seeds were removed, cracked, stratified and germinated as a group with the label "H8A". They were grown as seedlings on their own root in our greenhouse and upon reaching dormancy transplanted to a cultivated area of our experimental orchard located near Le Grand, Calif. in Merced County (San Joaquin Valley). During the summer of 2006 the claimed variety was selected by us as a single plant from the group of seedlings described above. Subsequent to origination of the present variety of plum tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, '19P442' (unpatented) plum tree, by being a medium to large size tree, by blooming in the mid season, by being self-unfruitful, and by producing fruit that is oblate in shape, black in skin color, and mostly red in flesh color, but is distinguished therefrom by producing fruit that is firmer in texture, sweeter in flavor, and that ripens about thirty days later.

The present variety is most similar to 'Blackred III' (U.S. Plant Pat. No. 18,668) interspecific tree, by having a vigorous tree, by being self-unfruitful, by being productive, and by producing fruit that is mostly black in skin color, that is mostly red in flesh color, that is firm in texture, that is clingstone in type, and that is sweet in flavor, but is distinguished therefrom by blooming about seven days later and by producing fruit that is somewhat smaller in size and that matures about ten days later.

SUMMARY OF VARIETY

The present plum variety is characterized by a medium to large size, vigorous, hardy, and very productive tree. Being self-unfruitful, the present variety requires cross pollination from another plum or interspecific tree that blooms during the mid to late season, such as 'Plumsweet V' interspecific tree (U.S. Plant Pat. No. 16,369). The present variety's moderate amount of blossoms and strong pollen production entices strong bee activity to facilitate pollination. The fruit matures under the ecological conditions described during the first week of August, with first picking on Aug. 1, 2018. The fruit is medium is size, very oblate in shape, black in skin color, clingstone in type, mostly red in flesh color, firm in texture, juicy, and very good in flavor.

DRAWING

The accompanying photograph exhibits four whole fruits positioned to display the characteristics of the skin color and form, one divided fruit to reveal the flesh and stone, typical leaves, and two insets depicting the flower buds and blossoms as they appeared on the tree during the blooming season.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif., and was developed at the state of firm ripe on Aug. 3, 2018, on a multiplied tree utilizing 'Nemaguard' rootstock (unpatented) during its tenth growing season. All major color code designations are by reference to the Inter-Society Color Council, National Bureau of Standards. Common color names are also used occasionally.

PARENTAGE

Seed parent: '19P442' (unpatented) plum tree.
Pollen parent: Unknown.

TREE

Size: Medium to large, reaching and maintaining a height of 9' [2.74 m.] and a spread of 10' [3.05 m.] after ten growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Pruned to a vase formed type.

Hardiness: Hardy with respect to central California winters.

Heat tolerance: Observed to perform adequately in typical central California climatic conditions, which typically include prolonged periods of heat.

Drought tolerance: Variety is developed for commercial orchards and requires regular irrigation.

Production: Productive, thinning usually necessary.

Fertility: Self-unfruitful, requiring cross pollination by a suitable mid to late seasonal blooming plum or interspecific, such as 'Plumsweet V' interspecific tree (U.S. Plant Pat. No. 16,369).

Bearing: Regular bearer, weather dependent, no crop failures observed as of yet.

Leaf bud burst: Late, toward the end of flowering.

Trunk:

*Size.*—Stocky, medium, reaching a maximum diameter of 5" [127 mm.] after ten growing seasons.

*Texture.*—Medium, shaggy.

*Bark Color.*—A Grayish brown [61. gy.Br] and Moderate brown [58. m.Br] variegation with Dark brown [59. d.Br] crevices present.

*Lenticels.*—Approximate Number Per Square Inch: 8. Color: Deep orange [51. deep O]. Typical Size: ¼" [6.4 mm.] in length. The width is typically one fourth as much as the length. Shape: Eye-shaped.

Branches:

*Size.*—Medium, diameter of the scaffold is 3½" [88.9 mm.] measured 12" above the crotch, diameter of limb is 1½" [38.1 mm.] measured 12" above the first fork.

*Texture.*—Medium, shaggy on first year wood, increasing roughness with age.

*Color.*—1st Year Wood Topside: Grayish red [19. gy.R]. 1st Year Wood Underside: Brilliant yellow green [116. brill.YG]. 2nd Year Wood: A Grayish brown [61. gy.Br] and Dark brown [59. d.Br] variegation with Light brown [57. l.Br] crevices present.

*Lenticels.*—Number Per Square Inch: About 40. Color: Strong brown [55. s.Br]. Typical size: Small, 1/32" [0.8 mm.] in length. The width is typically one fourth as much as the length. Shape: Eye-shaped.

Leaves:

*Size.*—Medium. Average Length: 3¾" [95.3 mm.]. Average Width: 1 13/16" [46.0 mm.].

*Arrangement.*—Alternate.

*Thickness.*—Medium.

*Form.*—Elliptical.

*Apex.*—Acuminate.

*Base.*—Mostly acute with an average base angle of seventy-five degrees.

*Surface.*—Smooth on both sides.

*Color.*—Dorsal Surface: Moderate olive green [125. m.OlG]. Ventral Surface: Moderate yellow green [120. m.YG].

*Red midvein.*—Absent.

*Margin.*—Finely serrate.

*Venation.*—Pinnately net veined.

*Petiole.*—Average Length: ½" [12.7 mm.]. Average Thickness: 1/16" [1.6 mm.]. Color: Grayish greenish yellow [105. gy.gY] and Grayish red [19. gy.R] where exposed to sunlight.

*Stipules.*—Number: 2 per leaf, up to 6 per growing tip. Average Length: ¼" [6.4 mm.]. Color: Brilliant yellow green [116. brill.YG] becoming Grayish red [19. gy.R] with age.

*Glands.*—Number: 1 to 2, most often 2. Position: Usually alternate, positioned on the petiole just below the leaf blade. Form: Globose. Size: Small, 1/64" [0.4 mm.] in diameter. Color: Brilliant yellow green [116. brill.YG] becoming Dark reddish brown [44. d.rBr] in the center with age.

*Leaf buds.*—Pointed.

Flower buds:

*Hardiness.*—Hardy, with respect to central California blooming season.

*Diameter.*—Typically 3/16" [4.8 mm.] 1 week before bloom.
*Length.*—Typically 5/16" [7.9 mm.] 1 week before bloom.
*Form.*—Not appressed.
*Surface.*—Slightly pubescent.
*Color.*—White [263. White].

Flowers: Perfect, complete, usually a single pistil, about twenty-five stamens, five sepals and petal locations alternately positioned.
*Average flower diameter.*—1 1/16" [27.0 mm.].
*Average flower depth.*—3/16" [4.8 mm.] when fully open.
*Average pedicel length.*—5/16" [7.9 mm.].
*Number of petals.*—Five, no double blossoms observed.
*Petal arrangement.*—Overlapping.
*Petal shape.*—Oval to slightly obovate.
*Petal margin.*—Entire, somewhat wavy.
*Average petal diameter.*—3/8" [9.5 mm.].
*Average petal length.*—7/16" [11.1 mm.].
*Petal apex.*—Rounded to slightly obovate.
*Petal base.*—Rounded to slightly cuneate.
*Petal color.*—White [263. White] on both sides.
*Anther color.*—Brilliant orange yellow [67. brill.OY].
*Pollen production.*—Abundant, bee enticing.
*Pollen color.*—Strong orange yellow [68. s.OY].
*Stigma color.*—Pale greenish yellow [104. p.gY].
*Stigma position.*—Stigma is located about 1/16" [1.6 mm.] below the average anther position.
*Ovary.*—Non-pubescent.
*Sepal color.*—Brilliant yellow green [116. brill.YG] on both sides.
*Sepal length.*—5/32" [4.0 mm.].
*Sepal width.*—1/8" [3.2 mm.].
*Sepal shape.*—Ovate.
*Sepal apex.*—Elliptical to match the width and length.
*Average pistil length.*—7/16" [11.1 mm.].
*Average stamen length.*—5/16" [7.9 mm.].
*Stamen position.*—Typically located about 1/64" [0.4 mm.] below the petals.
*Ovary.*—Smooth.
*Fragrance.*—Moderate in degree with a slight hint of vanilla.
*Blooming period.*—Medium compared with other varieties, about the same starting day as 'Blackred XII' interspecific tree (U.S. Plant Pat. No. 20,892).
*Onset of bloom.*—One percent on Feb. 27, 2018.
*Date of full bloom.*—Mar. 10, 2018.
*Duration of bloom.*—One to two weeks, dependent on ambient temperature.
*Bloom density.*—Medium.
*Number per cluster.*—Typically 2, up to 4 observed.

FRUIT

Maturity when described: Firm ripe, Aug. 3, 2018.
Date of first picking: Aug. 1, 2018.
Date of last picking: Aug. 20, 2018.
Size: Uniform, medium.
*Average diameter axially.*—2 3/16" [55.6 mm.].
*Average diameter across suture plane.*—2 3/4" [69.9 mm.].
*Average diameter across cheek plain.*—2 7/8" [73.0 mm.].
*Typical weight.*—5.7 ounces [161.6 grams].
Form: Uniform, symmetrical, very oblate.
*Axial view.*—Round.
*Longitudinal section form.*—Oblate.
Suture: A distinct Reddish black [24. rBlack] line located in a shallow trough extending from the base to the apex, with a slightly deeper groove at the base and a slight depression beyond the pistil point.
Suture depth: Very shallow from the apex to the shoulders, medium depth at the base.
Ventral surface: Rounded.
Lips: Fairly equal.
Cavity: Flaring, circular.
*Depth.*—1/2" [12.7 mm.].
*Breadth.*—15/16" [23.8 mm.].
*Stem markings.*—Rare, usually not present.
Base: Truncate, strongly cordate when viewed parallel to the suture.
Apex: Rounded.
Pistil point: An inconspicuous Light orange yellow [70. l.OY] dot depressed within the suture.
Stem: Medium size.
*Average length.*—3/8" [9.5 mm.].
*Average width.*—1/8" [3.2 mm.].
Skin:
*Thickness.*—Medium.
*Surface.*—Smooth.
*Tenacity.*—Tenacious to flesh.
*Astringency.*—Slight.
*Tendency to crack.*—None observed.
*Color.*—Blackish red [21. blackish R] over a Very dark red [17. v.d.R] background with very minor Light orange yellow [70. l.OY Y] freckling throughout.
*Lenticels.*—Number Per Square Inch: About 40. Average diameter: 1/80" [0.3 mm].
*Bloom.*—Heavy.
Flesh:
*Color.*—A Very red [11. v.R] toward the skin and Light yellow [86. l.Y] toward the stone with Pale yellow [89. p.Y] fibers toward the stone.
*Surface of pit cavity.*—Covered with Moderate yellow [87. m.Y] broken fibers when twisted away from stone.
*Amygdalin.*—Moderate to abundant.
*Juice.*—Abundant, rich.
*Texture.*—Medium, crisp.
*Fibers.*—Abundant, tender.
*Ripens.*—Fairly even.
*Flavor.*—A nice balance of acid and sugar, typically 16 to 17 brix.
*Aroma.*—Very slight.
*Eating quality.*—Very good.

STONE

Type: Clingstone.
Form: Oval.
Hilum: Narrow.
Base: Rounded.
Apex: Rounded with a short, sharp tip 1/16" [1.6 mm.] in length.
Sides: Fairly equal.
Surface: Rounded.
External color of stone: Dark orange yellow [72. d.OY].

Pit wall color when cracked: Light yellowish brown [76. l.yBr].
Cavity surface color: Strong yellowish brown [74. s.yBr].
Average pit wall thickness: 1/8" [3.2 mm.].
Average length: 1" [25.4 mm.].
Average width: 5/8" [15.9 mm.].
Average breadth: 3/8" [9.5 mm.].
Tendency to split: None observed.
Kernel:

*Form.*—Oval.
*Pellicle color.*—Dark yellowish brown [78. d.yBr].
*Skin color.*—Dark yellowish brown [78. d.yBr].
*Vein color.*—Deep yellowish brown [75. deep yBr].
*Taste.*—Bitter.
*Viable.*—Yes.
*Average Length.*—9/16" [14.3 mm.].
*Average Width.*—3/8" [9.5 mm.].

USE

Market: Fresh market and long distance shipping.
Keeping quality: Excellent. Fruit quality observed to remain in good condition after 30 days in standard cold room at 36° Fahrenheit [2° Celsius].
Shipping quality: Excellent.
Resistance to insects: Not tested.
Resistance to diseases: Not tested.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, *Prunus salicina*, substantially as illustrated and described, that is most similar to 'Blackred III' (U.S. Plant Pat. No. 18,668) interspecific tree, by having a vigorous tree, by being self-unfruitful, by being productive, and by producing fruit that is mostly black in skin color, that is mostly red in flesh color, that is firm in texture, that is clingstone in type, and that is sweet in flavor, but is distinguished therefrom by blooming about seven days later and by producing fruit that is somewhat smaller in size and that matures about ten days later.

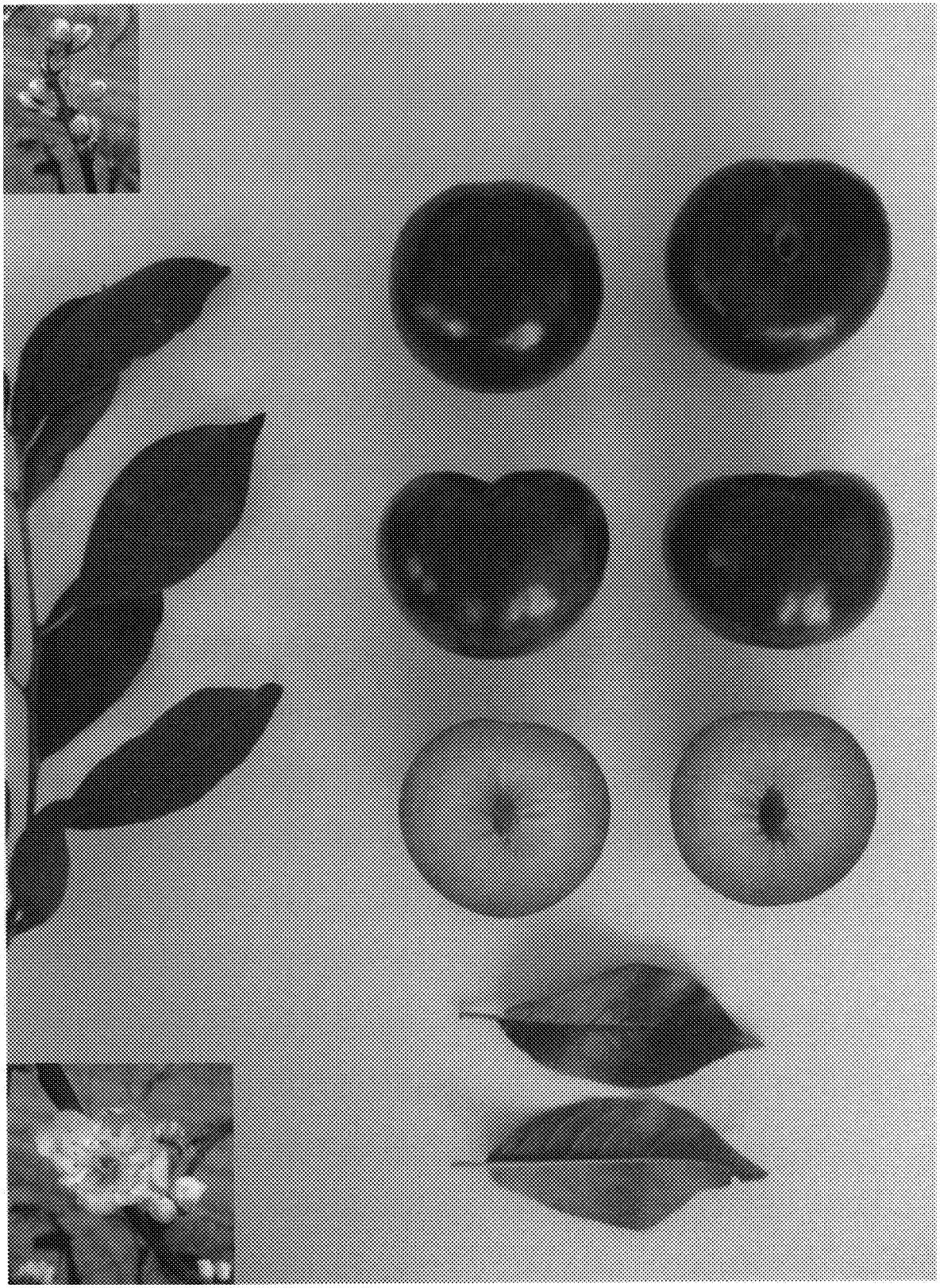

* * * * *